(12) United States Patent
Hofmann et al.

(10) Patent No.: US 8,124,711 B2
(45) Date of Patent: Feb. 28, 2012

(54) RU COMPLEXES, PRODUCTION AND USE THEREOF

(75) Inventors: Marco Hofmann, Burghausen (DE); Hans-Juergen Eberle, Munich (DE); Johann Weis, Sauerlach (DE)

(73) Assignee: Wacker Chemie AG, Munich (DE)

( * ) Notice: Subject to any disclaimer, the term of this patent is extended or adjusted under 35 U.S.C. 154(b) by 734 days.

(21) Appl. No.: 12/296,370

(22) PCT Filed: Mar. 28, 2007

(86) PCT No.: PCT/EP2007/052968
§ 371 (c)(1), (2), (4) Date: Oct. 7, 2008

(87) PCT Pub. No.: WO2007/118774
PCT Pub. Date: Oct. 25, 2007

(65) Prior Publication Data
US 2009/0171056 A1    Jul. 2, 2009

(30) Foreign Application Priority Data
Apr. 13, 2006 (DE) .......................... 10 2006 017 594

(51) Int. Cl.
*C08G 77/08* (2006.01)
(52) U.S. Cl. ................................. 528/15; 556/9; 556/12
(58) Field of Classification Search ................ 556/9, 12; 528/15
See application file for complete search history.

(56) References Cited

U.S. PATENT DOCUMENTS

| | | |
|---|---|---|
| 3,715,334 A | 2/1973 | Karstedt |
| 3,775,452 A | 11/1973 | Karstedt |
| 4,309,558 A | 1/1982 | Koga et al. |
| 5,248,802 A | 9/1993 | Bank |
| 5,559,284 A | 9/1996 | Matta et al. |
| 6,815,518 B2 | 11/2004 | Rhodia |
| 6,888,018 B2* | 5/2005 | Morita et al. .................... 556/11 |
| 7,803,893 B2* | 9/2010 | Hofmann et al. ............... 528/15 |
| 2003/0040181 A1 | 2/2003 | Antonelli |
| 2004/0092759 A1 | 5/2004 | Dilworth |
| 2010/0298588 A1* | 11/2010 | Touge et al. ..................... 556/12 |
| 2011/0009649 A1* | 1/2011 | Durand et al. ................. 549/469 |

FOREIGN PATENT DOCUMENTS

| | | |
|---|---|---|
| DE | 2810032 A | 9/1978 |
| EP | 0403706 A | 12/1990 |
| WO | WO 9605207 A | 2/1996 |
| WO | WO 2006018649 A | 2/2006 |

OTHER PUBLICATIONS

Berry et al., Organometallics 1994, 13, p. 2551-2553.
Walter Noll, Chemie and Technologie der Silicone, Verlag Chemie GmbH, Weinheim/Bergstr., 1968.
J. C. S. Chem. Communications, 1980, p. 661-663.
Pomeroy et al., J. Organomet. Chem. 1979, 177, C27-C28.
Science of Synthesis, Georg Thieme Verlag, Stuttgart, New York, 2001, vol. 1, p. 931-938.
Bogdan Marciniec et al., Comprehensive Handbook on Hydrosilylation, Oxford: Pergamon Press, 1992.
J. Y. Corey and J. Braddock-Wilking, Chem. Rev., 1999, 99, p. 175-292.

* cited by examiner

*Primary Examiner* — Margaret Moore
(74) *Attorney, Agent, or Firm* — Brooks Kushman P.C.

(57) ABSTRACT

Ruthenium compounds which have, in their ligand sphere, at least one $\eta^6$-bonded arene ligand and a silyl ligand; ruthenium complexes which have, in their ligand sphere, at least one $\eta^6$-bonded arene ligand to which is bonded a silyl or siloxy radical directly or via a spacer, and ruthenium complexes which have, in their ligand sphere, at least one $\eta^6$-bonded arene ligand and at least one further ligand to which is bonded a silyl or siloxy radical directly or via a spacer are useful as hydrosilylation catalysts.

8 Claims, No Drawings

RU COMPLEXES, PRODUCTION AND USE THEREOF

CROSS-REFERENCE TO RELATED APPLICATION

This application is the U.S. national phase of PCT Appln. No. PCT/EP2007/052968 filed Mar. 28, 2007 which claims priority to German application DE 10 2006 017 594.8 filed Apr. 13, 2006.

BACKGROUND OF THE INVENTION

1. Field of the Invention

The invention relates to the preparation of Ru complexes with silicophilic ligands and to the use thereof as catalysts in transition metal-catalyzed hydrosilylation.

2. Description of the Related Art

The addition of Si—H-functional compounds onto compounds with aliphatic unsaturated bonds, especially C=C double bonds (hydrosilylation), has already been known for some time.

Hydrosilylation allows Si-containing organic compounds, organosilanes and organopolysiloxanes to be prepared. It is used especially in the addition-crosslinking curing of organopolysiloxanes in the silicone industry, for example for the production of elastomers, molding materials in the dental industry or antiadhesive coatings in the paper and films industry.

The catalysts used most frequently for the hydrosilylation reaction are platinum and its compounds, the platinum being used in metallic form, as metal fixed on an inorganic support, as a platinum salt or in the form of a soluble or insoluble platinum complex.

To date, for the majority of the hydrosilylation reactions performed industrially, the so-called "Karstedt catalyst" known from U.S. Pat. No. 3,715,334 and U.S. Pat. No. 3,775,452 is used, which consists predominantly of a dimeric platinum-tetramethyldivinylsiloxane complex, which can be described by the formula $[Pt_2(TMDVS)_3]$ (TMDVS=tetramethyldivinyldisiloxane). The Karstedt catalyst is prepared proceeding from hexachloroplatinic acid $H_2PtCl_6$, which is likewise frequently used as a hydrosilylation catalyst in the form of an alcoholic solution.

Since platinum is one of the most expensive noble metals, there have already been frequent efforts to use other metals and compounds thereof as catalysts in hydrosilylation. For instance, the prior art already discloses the use of the other platinum group metals Pd, Rh, Ir, Ru in hydrosilylation. However, these have to date been described as alternatives to Pt in particular as catalysts for use in the case of specific substrates.

For example, US 2004/0092759 A1 and U.S. Pat. No. 5,559,264 describe Ru catalysts, for example $RuCl_3$, $RuBr_3$, $Ru(acac)_3$, Ru/C, $Ru_3(CO)_{12}$, $[RuCl_2(CO)_3]_2$, $[Ru(COD)Cl_2]_n$ (COD=1,5-cyclo-octadiene), $Ru(PPh_3)_2(CO)_2Cl_2$ and $Ru(PPh_3)_3(CO)H_2$ for the hydrosilylation of $HSi(R)_x(OR)_{3-x}$ (x=0-2) with an olefinic halide, such as allyl chloride.

EP 0403706 A2 describes the use of Ru complexes with at least one tertiary phosphine ligand, for example $Ru(CO)_3(PPh_3)_2$, $RuCl_2(PPh_3)_2$, $Ru(H)(Cl)(PPh_3)_3$, $Ru(PPh_3)_4H_2$ and $Ru(CH_2=CH_2)(PPh_3)_3$ as catalysts for the hydrosilylation of allylamines with SiH-functional silanes.

U.S. Pat. No. 5,248,802 describes the hydrosilylation of trichlorosilane with olefinic nitriles, for example acrylonitrile, in the presence of Ru-halogen or Ru-phosphine compounds, such as $RuCl_3$, $RuBr_3$, $RuI_3$, $Ru(CO)_3(PPh_3)_2$, $RuCl_2(PPh_3)_3$, $Ru(H)(Cl)(PPh_3)_3$, $RuH_2(PPh_3)_4$, $Ru(CH_2=CH_2)(PPh_3)_3$ and $RuCl_2(CO)_2(PPh_3)_2$.

Finally, DE 2810032 A1 describes the hydrosilylation of dichlorosilane with olefins in the presence of Ru complexes, for example $RuCl_2(PPh_3)_3$, $Ru(H)(Cl)(PPh_3)_3$, $RuH_3(PPh_3)_3[Si(OMe)_3]$, $RuH_3(PPh_3)_3[Si(OMe)_2Ph]$ and $RuH_2(PPh_3)_4$.

However, the use of other compounds with transition metals, such as Ni, Co or Fe, as catalysts for hydrosilylations has also already been described.

In general, these catalysts, however, are distinctly inferior to the common Pt catalysts with regard to reactivity and selectivity; especially for the crosslinking of polysiloxanes by means of a hydrosilylation reaction, the rate and selectivity of the non-Pt catalysts described to date for the hydrosilylation is generally insufficient. From an economic point of view too, these systems are usually not necessarily advantageous, since higher catalyst concentrations have to be employed for the non-platinum catalysts, and, in the case of rhodium, even higher costs than for platinum are to be expected.

SUMMARY OF THE INVENTION

It was thus an object of the invention to provide an alternative hydrosilylation catalyst. More particularly, it was an object of the invention to provide a catalyst which is superior both from an economic point of view and with regard to reactivity and selectivity to the non-platinum hydrosilylation catalysts described to date in the prior art and thus constitutes an alternative to the Pt catalysts known from the prior art. It has surprisingly been found that these and other objects are achieved by a particular class of Ru complexes which, in their ligand sphere, have one or more silicophilic ligands and an $\eta^6$-bonded arene ligand. The $\eta^6$-bonded arene ligand may also itself be the silicophilic ligand.

Silicophilic ligands are understood hereinafter to mean
(a) silyl ligands bound or coordinated directly to the ruthenium center; or
(b) other ligands which are bound or coordinated to the ruthenium center and in turn bear silyl and/or siloxy substituents.

The silyl or siloxy substituents present on the ligand coordinated to the ruthenium in the group (b) of silicophilic ligands may be in the α-position to the coordination site of the ligand or be bonded thereto via a spacer. The ligands are preferably carbon n-bonded (olefinic, unsaturated) ligands. Among the group (b) of silicophilic ligands, especially $\eta^6$-bonded arene ligands substituted by silyl or siloxy substituents should be emphasized, where the silyl or siloxy substituents may be bonded to the arene directly or via an additional spacer. Such substituents simultaneously constitute the inventive $\eta^6$-bonded arene ligand and the silicophilic ligand combined in one ligand in the ligand sphere of the ruthenium.

Equally, in the case of presence of silicophilic ligands of group (a), the $\eta^6$-bonded arene ligand present in accordance with the invention may optionally also simultaneously be a ligand of group (b).

The invention provides a process for hydrosilylation (hydrosilylation process) in the presence of a ruthenium catalyst, characterized in that the ruthenium catalyst is selected from the group comprising ruthenium complexes which have, in their ligand sphere, at least one $\eta^6$-bonded arene ligand and a silyl ligand; ruthenium complexes which have, in their ligand sphere, at least one $\eta^6$-bonded arene ligand to which is bonded a silyl or siloxy radical directly or via a spacer, and ruthenium complexes which have, in their ligand sphere, at least one η⁶-bonded arene ligand and at least one further ligand to which is bonded a silyl or siloxy radical directly or via a spacer.

The invention further provides for the use of ruthenium compounds selected from the group comprising ruthenium complexes which have, in their ligand sphere, at least one η⁶-bonded arene ligand and a silyl ligand; ruthenium complexes which have, in their ligand sphere, at least one η⁶-bonded arene ligand to which is bonded a silyl or siloxy radical directly or via a spacer, and ruthenium complexes which have, in their ligand sphere, at least one η⁶-bonded arene ligand and at least one further ligand to which is bonded a silyl or siloxy radical directly or via a spacer as hydrosilylation catalysts.

The ruthenium center in these complexes may in principle be present in all oxidation states common for organometallic ruthenium complexes, especially in the 0, +II, +III, +IV oxidation states. Preference is given to complexes with the 0, +II and +IV oxidation states of ruthenium.

The use of the inventive compounds as catalysts in hydrosilylation is notable especially for the fact that the catalysts are very active, selective and universally usable catalysts which are nevertheless free of platinum.

The silicophilic ligands of the catalyst make the compound silicone-like, thus leading to the effect that the catalyst is generally completely miscible into silanes, siloxanes or polysiloxanes to be hydrosilylated and hence result in completely homogeneous reaction mixtures. This leads to a high activity of the compounds. Associated with this high activity is generally additionally also a high hydrosilylation selectivity in the sense of a comparatively low level of side reactions, such as hydrogenation or dehydrogenating silylation with simultaneously moderate catalyst concentrations needed.

One possible embodiment of Ru complexes for the inventive use with silyl ligands bonded or coordinated directly to the ruthenium center is that of compounds of the general formula (1)

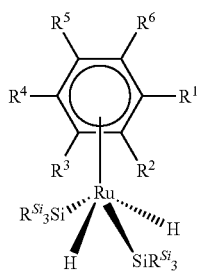

formula (1)

where
the two SiR$^{Si}_3$ radicals may be the same or different and R$^{Si}_3$ overall is a radical selected from the group comprising trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, Me(OSiMe₃)₂, Ph(OSiMe₃)₂, (OSiMe₃)₃, (dialkylsiloxy)$_n$-SiMe₃, (diarylsiloxy)$_n$-SiMe₃ and [alkyl(aryl)siloxy]$_n$-SiMe₃, where n in each case is from 1 to 500; and the R¹ to R⁶ radicals are each independently selected from the group comprising hydrogen (H), alkyl, aryl and alkoxy, SiR$^{Si}_3$ and OSiR$^{Si}_3$, with the proviso that the alkyl, aryl and alkoxy radicals may optionally in turn be substituted by SiR$^{Si}_3$ and OSiR$^{Si}_3$ radicals where R$^{Si}_3$ here is as defined above; and two adjacent R¹ to R⁶ radicals may optionally form a further ring, for example a naphthyl radical.

When R¹ to R⁶ in the compounds of the general formula (1) are radicals substituted by SiR$^{Si}_3$ and OSiR$^{Si}_3$ radicals, they are preferably selected from the group comprising —(CH₂)$_m$—SiR$^{Si}_3$, —O—SiR$^{Si}_3$, —O(CH₂)$_n$—SiR$^{Si}_3$, —(CH₂)$_m$—OSiR$^{Si}_3$ and —O(CH₂)$_m$—OSiR$^{Si}_3$, where m is an integer from 1 to 3 and R$^{Si}_3$ is as defined above.

Compounds of the general formula (1) in which R$^{Si}_3$ overall is a trialkyl radical are already known from the prior art as (η⁶-arene)Ru(H)₂(SiR₃)₂ where η⁶-arene=C₆H₆, C₆Me₆, p-Me-C₆H₄-iPr, and R₃=Me₃, or where η⁶-arene=C₆H₆ and R₃=Et₃, from Berry et al., Organometallics 1994, 13, 2551-2553.

The invention further provides compounds of the general formula (1a)

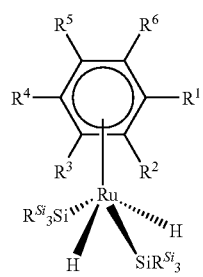

formula (1a)

where the two SiR$^{Si}_3$ radicals may be the same or different and R$^{Si}_3$ overall is a radical selected from the group comprising triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, Me(OSiMe₃)₂, Ph(OSiMe₃)₂, (OSiMe₃)₃, (dialkylsiloxy)$_n$-SiMe₃, (diarylsiloxy)$_n$-SiMe₃ and [alkyl(aryl)siloxy]$_n$-SiMe₃, where n in each case is from 1 to 500; and the R¹ to R⁶ radicals are each independently selected from the group comprising hydrogen (H), alkyl, aryl and alkoxy, SiR$^{Si}_3$ and OSiR$^{Si}_3$, with the proviso that the alkyl, aryl and alkoxy radicals may optionally in turn be substituted by SiR$^{Si}_3$ and OSiR$^{Si}_3$ radicals where R$^{Si}_3$ here is selected from the group specified above and additionally trialkyl; and two adjacent R¹ to R⁶ radicals may optionally form a further ring, for example a naphthyl radical.

When R¹ to R⁶ in the compounds of the general formula (1a) are radicals substituted by SiR$^{Si}_3$ and OSiR$^{Si}_3$ radicals, they are preferably selected from the group comprising —(CH₂)$_m$—SiR$^{Si}_3$, —O—SiR$^{Si}_3$, —O(CH₂)$_m$—SiR$^{Si}_3$, —(CH₂)$_m$—OSiR$^{Si}_3$ and —O(CH₂)$_m$—OSiR$^{Si}_3$, where m is an integer from 1 to 3 and R$^{Si}_3$ is defined as specified for the general formula (1a).

Preferred radicals for SiR$^{Si}_3$ are selected from the group comprising Me(OSiMe₃)₂, (dialkylsiloxy)$_n$-SiMe₃, (diarylsiloxy)$_n$-SiMe₃ and [alkyl(aryl)siloxy]$_n$-SiMe₃, where n is in each case from 1 to 500. The R¹ to R⁶ radicals are preferably selected from hydrogen (H) and alkyl.

Specific, particularly preferred embodiments for the inventive use and for the inventive compounds are the following compounds of the formulae (1b), (1c) and (1d).

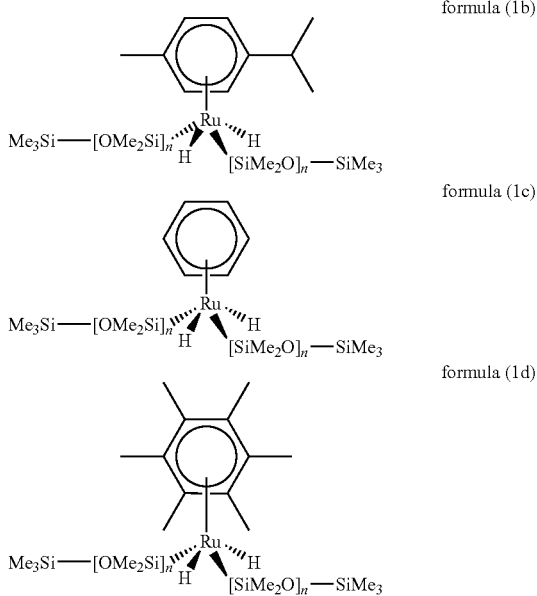

formula (1b)

formula (1c)

formula (1d)

where n in each case is from 1 to 500.

An alternative possible embodiment of Ru complexes for the inventive use with silyl ligands bonded or coordinated directly to the ruthenium center is that of compounds of the general formula (2)

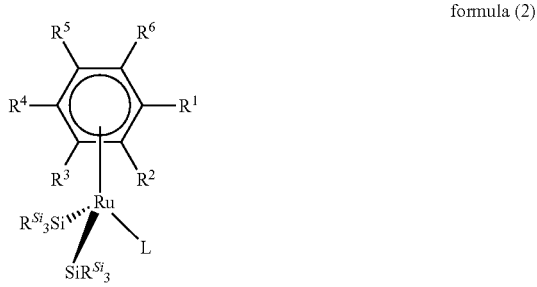

formula (2)

where
the two SiR$^{Si}_3$ radicals may be the same or different and R$^{Si}_3$ overall is a radical selected from the group comprising trialkyl, triaryl, dialkylhalogen, diarylhalogen, alkyl(aryl)halogen, alkyldihalogen, aryldihalogen, trihalogen, dialkyl (alkoxy), diaryl(alkoxy), alkyl(aryl)alkoxy, alkyl(dialkoxy), aryl(dialkoxy), trialkoxy, Me(OSiMe$_3$)$_2$, Ph(OSiMe$_3$)$_2$, (OSiMe$_3$)$_3$, (dialkylsiloxy)$_n$-SiMe$_3$, (diarylsiloxy)$_n$-SiMe$_3$ and [alkyl(aryl)siloxy]$_n$-SiMe$_3$, where n in each case is from 1 to 500; and
the R$^1$ to R$^6$ radicals are each independently selected from the group comprising hydrogen (H), alkyl, aryl and alkoxy, SiR$^{Si}_3$ and OSiR$^{Si}_3$, with the proviso that the alkyl, aryl and alkoxy radicals may optionally in turn be substituted by SiR$^{Si}_3$ and OSiR$^{Si}_3$ radicals where R$^{Si}_3$ is as defined above; and
two adjacent R$^1$ to R$^6$ radicals may optionally form a further ring, for example a naphthyl radical; and
L is an uncharged 2-electron donor ligand.

Preferred embodiments of the uncharged 2-electron donor ligands L are CO and phosphines, especially trialkyl- or triarylphosphines.

When R$^1$ to R$^6$ in the compounds of the general formula (2) are radicals substituted by SiR$^{Si}_3$ and OSiR$^{Si}_3$ radicals, they are preferably selected from the group comprising —(CH$_2$)$_m$—SiR$^{Si}_3$, —O—SiR$^{Si}_3$, —O(CH$_2$)$_m$—SiR$^{Si}_3$, —(CH$_2$)$_m$—OSiR$^{Si}_3$ and —O(CH$_2$)$_m$—OSiR$^{Si}_3$, where m is an integer from 1 to 3 and R$^{Si}_3$ is as defined above.

Compounds of the general formula (2) in which R$^{Si}_3$ overall is a trihalogen radical and L=CO are already known from the prior art as ($\eta^6$-arene)Ru(CO) (SiCl$_3$)$_2$ where $\eta^6$-arene=C$_6$H$_5$Me, C$_6$H$_4$Me$_2$, C$_6$H$_3$Me$_3$, C$_6$H$_2$Me$_4$, C$_6$Me$_6$, C$_6$H$_5$tBu, p-C$_6$H$_4$-tBu$_2$, C$_6$H$_5$Cl from Pomeroy et al., J. Organomet. Chem. 1979, 177, C27-C28; Chemical Communications 1980, 661-663.

The invention further provides compounds of the general formula (2a)

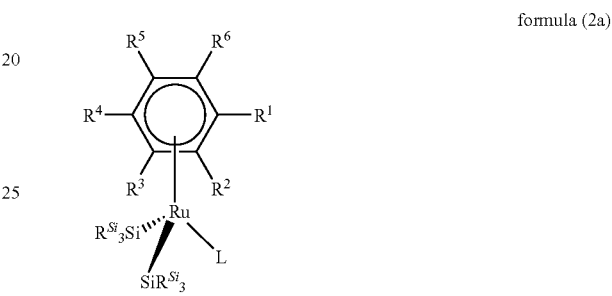

formula (2a)

where
the two SiR$^{Si}_3$ radicals may be the same or different and R$^{Si}_3$ overall is a radical selected from the group comprising trialkyl, triaryl, dialkylhalogen, diarylhalogen, alkyl(aryl)halogen, alkyldihalogen, aryldihalogen, dialkyl(alkoxy), diaryl (alkoxy), alkyl(aryl)alkoxy, alkyl(dialkoxy), aryl(dialkoxy), trialkoxy, Me(OSiMe$_3$)$_2$, Ph(OSiMe$_3$)$_2$, (OSiMe$_3$)$_3$, (dialkylsiloxy)$_n$-SiMe$_3$, (diarylsiloxy)$_n$-SiMe$_3$ and [alkyl(aryl)siloxy]$_n$-SiMe$_3$, where n in each case is from 1 to 500; and
the R$^1$ to R$^6$ radicals are each independently selected from the group comprising hydrogen (H), alkyl, aryl and alkoxy, SiR$^{Si}_3$ and OSiR$^{Si}_3$, with the proviso that the alkyl, aryl and alkoxy radicals may optionally in turn be substituted by SiR$^{Si}_3$ and OSiR$^{Si}_3$ radicals where R$^{Si}_3$ here is selected from the group specified above and additionally trihalogen; and
two adjacent R$^1$ to R$^6$ radicals may optionally form a further ring, for example a naphthyl radical; and
L is an uncharged 2-electron donor ligand.

Preferred embodiments of a 2-electron donor ligand L are CO and phosphines, especially trialkyl- or triaryl-phosphines.

When R$^1$ to R$^6$ in the compounds of the general formula (2a) are radicals substituted by SiR$^{Si}_3$ and OSiR$^{Si}_3$ radicals, they are preferably selected from the group comprising —(CH$_2$)$_m$—SiR$^{Si}_3$, —O—SiR$^{Si}_3$, —O(CH$_2$)$_m$—SiR$^{Si}_3$, —(CH$_2$)$_m$—OSiR$^{Si}_3$ and —O(CH$_2$)$_m$—OSiR$^{Si}_3$, where m is an integer from 1 to 3 and R$^{Si}_3$ is defined as specified for the compounds of the general formula (2a).

Preferred radicals for SiR$^{Si}_3$ are selected from the group comprising Me(OSiMe$_3$)$_2$, (dialkylsiloxy)$_n$-(SiMe$_3$, (diarylsiloxy)$_n$-SiMe$_3$ and [alkyl(aryl)siloxy]$_n$-SiMe$_3$, where n is in each case from 1 to 500. The R$^1$ to R$^6$ radicals are preferably selected from hydrogen (H) and alkyl. Preferably, L is selected from the group comprising CO, PPh$_3$ and PMe$_3$.

Specific, particularly preferred embodiments for the inventive use and for the inventive compounds are the following compounds of the formulae (2b), (2c) and (2d).

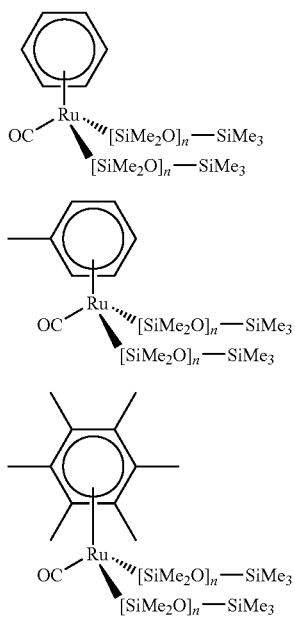

where n in each case is from 1 to 500.

In the case that no silyl ligands bonded or coordinated directly to the ruthenium center are present, the inventive silyl and/or siloxy substituents may in principle be bonded to any ligands for ruthenium as substituents which are known to the skilled person from the prior art. Particular preference is given to the presence of the silyl and/or siloxy substituents directly on the inventive $\eta^6$-bonded arene ligands. Possible embodiments of such Ru complexes are compounds of the general formulae (3a), (3b), (3c) and (3d)

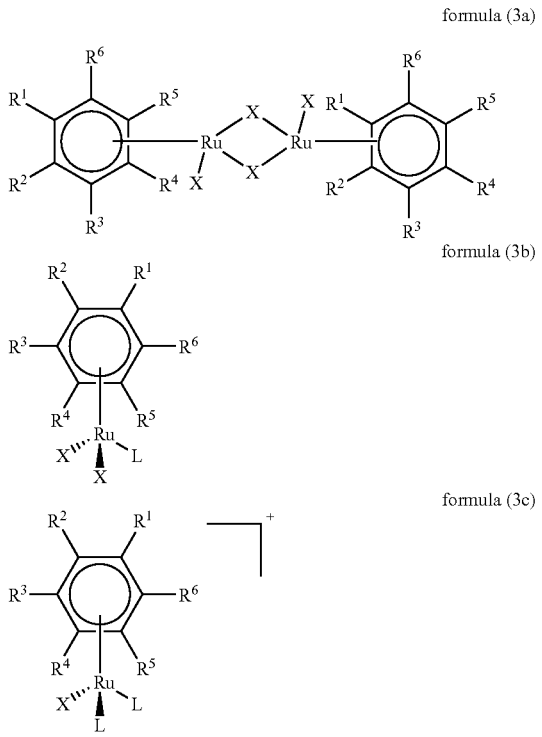

where

X is an anionic ligand, especially selected from the group comprising hydride (H), halide, alkoxy, siloxy, acetate and trifluoroacetate; and L is an uncharged 2-electron donor ligand, preferably selected from the group comprising N-functional ligands, especially nitriles and pyridines; P-functional ligands, especially tertiary phosphines, for example trialkyl- and triarylphosphines, ditertiary phosphines, for example bis(diphenylphosphino)methane (dppm) and bis(diphenylphosphino)ethane (dppe); tertiary arsines; tertiary stibines; oxygen ligands, for example acetone; sulfur ligands, for example DMSO, and carbon ligands, for example CO and isonitriles; and L and X are optionally joined to one another and, together with the ruthenium atom to which they are bonded, may form a ring which may contain further atoms, the $R^1$ to $R^6$ radicals are each independently selected from the group comprising hydrogen (H), alkyl, aryl, alkoxy, halogen, $SiR^{Si}_3$ and $OSiR^{Si}_3$, where the alkyl, aryl and alkoxy radicals may optionally in turn be substituted by $SiR^{Si}_3$ and $OSiR^{Si}_3$ radicals, and combined with the proviso that at least one of the $R^1$ to $R^6$ radicals is an $SiR^{Si}_3$ radical, an $OSiR^{Si}_3$ radical or an alkyl, aryl or alkoxy radical substituted by $SiR^{Si}_3$, $OSiR^{Si}_3$; and $SiR^{Si}_3$ and/or $OSiR^{Si}_3$ radicals present may be the same or different, where $R^{Si}_3$ overall is a radical selected from the group comprising trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, $(dialkylsiloxy)_n$-$SiMe_3$, $(diarylsiloxy)_n$-$SiMe_3$ and $[alkyl(aryl)siloxy]_n$-$SiMe_3$, where n in each case is from 1 to 500.

When $R^1$ to $R^6$ in the compounds of the general formula (3a), (3b), (3c) and (3d) are radicals substituted by $SiR^{Si}_3$ and $OSiR^{Si}_3$ radicals, they are preferably selected from the group comprising —$(CH_2)_m$—$SiR^{Si}_3$, —O—$SiR^{Si}_3$, —O$(CH_2)_m$—$SiR^{Si}_3$, —$(CH_2)_m$—$OSiR^{Si}_3$ and —O$(CH_2)_m$—$OSiR^{Si}_3$, where m is an integer of 1 to 3 and $R^{Si}_3$ is as defined above.

Preferably, in the compounds of the general formula (3a), (3b), (3c) and (3d), one $R^1$ to $R^6$ radical (in the case of compounds of the general formula (3a), in each case one $R^1$ to $R^6$ radical per arene ligand) is an $SiR^{Si}_3$, $OSiR^{Si}_3$ or an alkyl, aryl and alkoxy radical substituted by $SiR^{Si}_3$, $OSiR^{Si}_3$, especially of the preferred embodiment specified.

In the case of cationic complexes, such as those of the general formula (3c) and (3d), in addition to halide, it is possible to use noncoordinating or weakly coordinating anions, especially selected from the group comprising $BF_4^-$, $PF_6^-$, $BPh_4^-$.

One possible embodiment in which L and X are joined to one another and, together with the ruthenium atom to which they are bonded, form a ring would be an acetylacetonato ligand.

One possible particularly preferred embodiment of a compound of the general formula (3a) is a compound of the formula (3e)

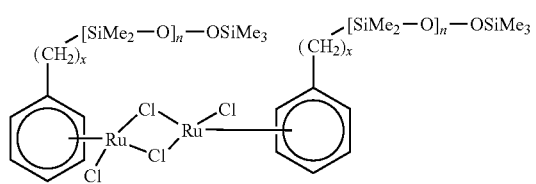
formula (3e)

where x is from 0 to 3; and
n is from 1 to 500.

A further preferred embodiment of inventive Ru complexes in which no silyl ligands bonded or coordinated directly to the ruthenium center are present is that of $\eta^2$-bonded olefinic ligands with silyl substituents of the general formula (4)

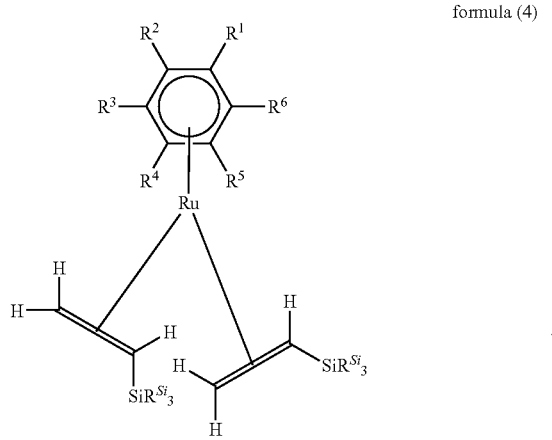
formula (4)

where
the two $SiR^{Si}_3$ radicals may be the same or different, where $R^{Si}_3$ overall is a radical selected from the group comprising trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, $(dialkylsiloxy)_n-SiMe_3$, $(diarylsiloxy)_n-SiMe_3$ and $[alkyl(aryl)siloxy]_n-SiMe_3$, where n in each case is from 1 to 500;
and the two $SiR^{Si}_3$ radicals may optionally be joined to one another via an $R^{Si}$ substituent in each case; and
the $R^1$ to $R^6$ radicals are each independently selected from the group comprising hydrogen (H), alkyl, aryl and alkoxy, $SiR^{Si}_3$ and $OSiR^{Si}_3$, with the proviso that the alkyl, aryl and alkoxy radicals may optionally in turn be substituted by $SiR^{Si}_3$ and $OSiR^{Si}_3$ radicals, where $R^{Si}_3$ is as defined above; and
two adjacent $R^1$ to $R^6$ radicals may optionally form a further ring, for example a naphthyl radical.

Possible preferred embodiments are compounds of the general formulae (4a), (4b) and (4c)

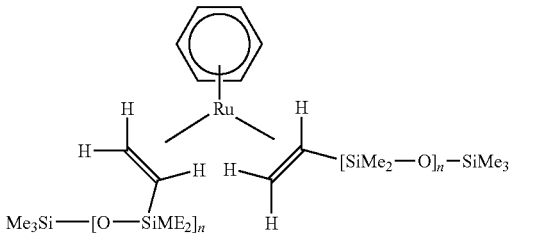
formula (4a)

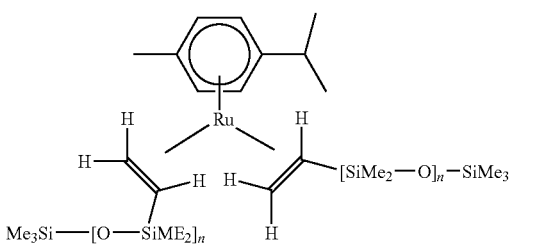
formula (4b)

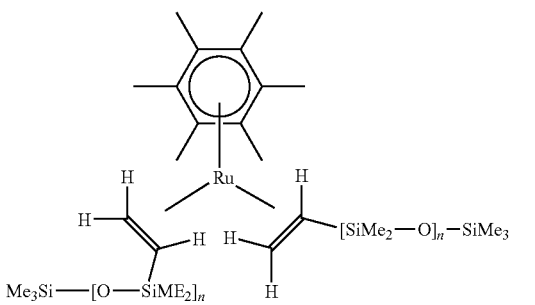
formula (4c)

where n is from 1 to 500.
A particularly preferred embodiment in which the two $SiR^{Si}_3$ radicals are optionally joined to one another via in each case one $R^{Si}$ substituent via an oxygen atom and thus form a bidentate divinylsiloxane ligand is that of compounds of the general formla (5)

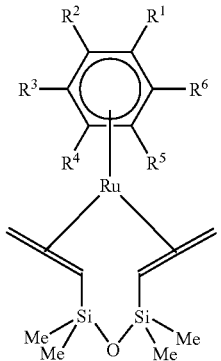
formula (5)

where
the $R^1$ to $R^6$ radicals are each independently selected from the group comprising hydrogen (H), alkyl, aryl, alkoxy, $SiR^{Si}_3$ and $OSiR^{Si}_3$, where the alkyl, aryl and alkoxy radicals may optionally in turn be substituted by $SiR^{Si}_3$ and $OSiR^{Si}_3$ radicals; and
where $R^{Si}_3$ overall is a radical selected from the group comprising trialkyl, triaryl, dialkylhalogen, diarylhalogen, alkyl (aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, Me(OSiMe$_3$)$_2$, Ph(OSiMe$_3$)$_2$, (OSiMe$_3$)$_3$, (dialkylsiloxy)$_n$-SiMe$_3$, (diarylsiloxy)$_n$-SiMe$_3$ and [alkyl(aryl)siloxy]$_n$-SiMe$_3$, where n in each case is from 1 to 500; and two adjacent R$^1$ to R$^6$ radicals may optionally form a further ring, for example a naphthyl radical.

When R$^1$ to R$^6$ in the compounds of the general formulae (4) and (5) are radicals substituted by SiR$^{Si}_3$ and OSiR$^{Si}_3$ radicals, they are preferably selected from the group comprising —(CH$_2$)$_m$—SiR$^{Si}_3$, —O—SiR$^{Si}_3$, —O(CH$_2$)$_m$—SiR$^{Si}_3$, —(CH$_2$)$_m$—OSiR$^{Si}_3$ and —O(CH$_2$)$_m$—OSiR$^{Si}_3$, where m is an integer of 1 to 3 and R$^{Si}_3$ is in each case as defined above.

Possible preferred embodiments are compounds of the formulae (5a), (5b) and (5c).

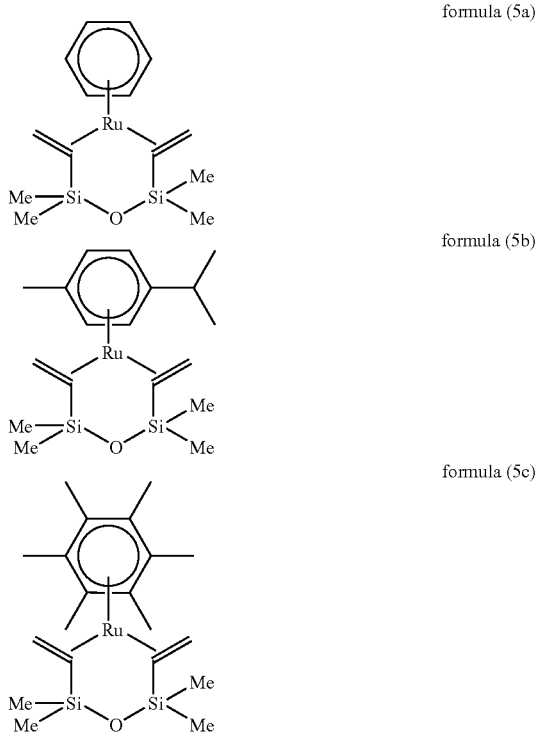

formula (5a)

formula (5b)

formula (5c)

The statements which follow apply equally to all embodiments specified herein, especially to the compounds of the general formulae (1), (1a), (1b), (1c), (1d), (2), (2a), (2b), (2c), (2d), (3a), (3b), (3c), (3d), (3e), (4), (4a), (4b), (4c), (5), (5a), (5b) and (5c).

Particular preference is given to uncharged complexes for the inventive use and for use in the process according to the invention.

Particular preference is given to complexes in which R$^{Si}_3$ is a radical selected from the group comprising Me(OSiMe$_3$)$_2$, Ph(OSiMe$_3$)$_2$, (OSiMe$_3$)$_3$, (dialkylsiloxy)$_n$-SiMe$_3$, (diarylsiloxy)$_n$-SiMe$_3$ and [alkyl(aryl)siloxy]$_n$-SiMe$_3$ radical, where n in each case is from 1 to 500, since these complexes have a high similarity to siloxanes. The particular advantage of such Ru compounds is their good solubility in polysiloxanes, as are used in the crosslinking reaction of silicones.

n is generally from 1 to 500. n is preferably from 1 to 250, more preferably from 10 to 200.

Preference is given to selecting the R$^1$ to R$^6$ radicals from the group comprising hydrogen (H), alkyl radicals and alkyl radicals substituted by SiR$^{Si}_3$ radicals, where R$^{Si}_3$ is in turn selected from the above-mentioned preferred radicals.

The inventive Ru complexes can be synthesized by standard methods known in principle to the person skilled in the art from the prior art.

Inventive compounds which have, directly in their ligand sphere, a silyl ligand (direct Ru—Si bond), especially those compounds of the general formulae (1) and (2), can be obtained either via (a) oxidative addition of SiH-functional silanes and siloxanes onto suitable arene-Ru precursors (for example according to J. Y. Corey, J. Braddock-Wilking, Chem. Rev. 1999, 99, 175-292); or (b) oxidative addition of SiH-functional silanes and siloxanes onto suitable Ru precursors and subsequent ligand/arene exchange, as described in Science of Synthesis, 2001, Georg Thieme Verlag, Stuttgart, New York, volume 1, p. 931-936.

The inventive compounds which have, in their ligand sphere, ligands which in turn bear silyl and/or siloxy substituents, especially those compounds of the general formulae (3) to (5), can be obtained by reaction of common ruthenium precursors—optionally with simultaneous reduction of the Ru precursor with a suitable reducing agent, especially zinc, magnesium and ethanol (with Na$_2$CO$_3$—with appropriate ligands into which appropriate substituents have been introduced by means of standard organosilicon chemistry methods, especially by means of metathesis reactions using Grignard reagents, lithium organyls, hydrosilylations or Birch reductions. Ruthenium-vinylsilane or -siloxane compounds of the general formula (4) and (5) can also be prepared via ligand exchange processes with the appropriate vinylsilanes and -siloxanes, optionally with reduction of the Ru precursor with a suitable reducing agent, especially zinc, magnesium and ethanol (with Na$_2$CO$_3$).

The inventive catalysts, especially those of the general formulae (1) to (5), are used generally in such an amount as to result in an Ru content of 10-1000 ppm, preferably 50-500 ppm, based on the total mass of the reacting substrates.

The hydrosilylation reactions using the inventive catalysts are effected generally at temperatures between room temperature, especially 20° C., and 200° C., preferably between 50° C. and 160° C., and a pressure of 900 to 1100 hPa. However, it is also possible to employ higher or lower temperatures and pressures.

The hydrosilylation reactions can be performed either under air or under an inert gas atmosphere (nitrogen, argon), preference being given to reaction under inert gas atmosphere.

The process according to the invention and the inventive use of the ruthenium catalysts can generally be effected in all hydrosilylation reactions which are known to the person skilled in the art from the prior art and are described, for example, in Walter Noll "Chemie und Technologie der Silicone" [Chemistry and Technology of the Silicones], Verlag Chemie GmbH, Weinheim/Bergstr. 1968; Bogdan Marciniec, "Comprehensive Handbook on Hydrosilylation", Oxford: Pergamon Press, 1992, and they are generally used in all hydrosilylatable, especially crosslinkable, compositions known from the prior art.

The inventive use of the catalysts and the process according to the invention are suitable both for the synthesis of low molecular weight compounds and for the curing of higher molecular weight compounds, especially of polymers with unsaturated groups, especially with carbon-carbon double bonds.

In particular, those hydrosilylation reactions in which C═C-functional polysiloxanes are reacted with SiH-functional polysiloxanes or C═C-functional organosilanes are reacted with SiH-functional organosilanes are catalyzed.

Preference is given in particular to the reaction of vinyl-terminal polydimethylsiloxanes with SiH-functional polysiloxanes of the general formula $Me_3SiO—[Si(H)(Me)O]_x$—$SiMe_3$, where x is from 1 to 500, especially from 1 to 100, and of Si-vinyl-functional organosilanes with Si—H-functional organosilanes.

Specific examples of Si-vinyl-functional organosilanes which can be hydrosilylated by the process according to the invention or with the inventive use of the catalysts include vinyltrimethylsilane, vinyltriethoxy-silane, vinylmethyldiethoxysilane, vinylmethyldimeth-oxysilane, vinyltrichlorosilane.

Specific examples of SiH-functional organosilanes include $HSi(OR')_3$ where R' is an alkyl radical, $HSi(Me)_{3-x}Cl_x$ where x is from 1 to 3, and $HSiR''_3$ where R'' is an alkyl or aryl radical.

The invention further relates to hydrosilylatable compositions comprising
(A) a compound with at least one aliphatically unsaturated carbon-carbon bond,
(B) a compound with at least one silicon-hydrogen bond and
(D) a ruthenium compound, characterized in that the ruthenium compound is selected from the group comprising ruthenium complexes which have, in their ligand sphere, at least one $\eta^6$-bonded arene ligand and a silyl ligand; ruthenium complexes which have, in their ligand sphere, at least one $\eta^6$-bonded arene ligand to which is bonded a silyl or siloxy radical directly or via a spacer, and ruthenium complexes which have, in their ligand sphere, at least one $\eta^6$-bonded arene ligand and at least one further ligand to which is bonded a silyl or siloxy radical directly or via a spacer.

A preferred embodiment of the hydrosilylatable compositions concerns polyorganosiloxane compositions comprising
(A) polyorganosiloxanes which have radicals with aliphatic carbon-carbon multiple bonds,
(B) polyorganosiloxanes with Si-bonded hydrogen atoms or instead of (A) and (B)
(C) polyorganosiloxanes which comprise SiC-bonded radicals with aliphatic carbon-carbon multiple bonds and Si-bonded hydrogen atoms, and
(D) a ruthenium compound, characterized in that the ruthenium compound is selected from the group comprising ruthenium complexes which have, in their ligand sphere, at least one $\eta^6$-bonded arene ligand and a silyl ligand; ruthenium complexes which have, in their ligand sphere, at least one $\eta^6$-bonded arene ligand to which is bonded a silyl or siloxy radical directly or via a spacer, and ruthenium complexes which have, in their ligand sphere, at least one $\eta^6$-bonded arene ligand and at least one further ligand to which is bonded a silyl or siloxy radical directly or via a spacer.

The ruthenium compound of component (D) functions in each case as a hydrosilylation catalyst (ruthenium catalyst). Preference is given to using compounds of the general formula (1) to (5), especially one or more of the above-specified embodiments.

Hydrosilylatable compositions are especially crosslinkable compositions.

Components (A), (B) and (C) described for the hydrosilylatable compositions correspond to the compounds (reactants) to be converted in the process according to the invention. Both the inventive compositions and the processes according to the invention and the use are based on the same inventive ruthenium catalysts.

The process according to the invention for hydrosilylation is carried out by supplying energy, especially by supplying heat. The same applies to the inventive hydrosilylatable compositions.

The inventive hydrosilylatable compositions preferably comprise compounds which have at least one aliphatically unsaturated carbon-carbon bond and are selected from the group comprising vinyl-functional organosilanes and vinyl-terminal polydimethylsiloxanes, and compounds having at least one silicon-hydrogen bond which are selected from the group comprising SiH-functional polysiloxanes and Si—H-functional organosilanes.

The invention likewise relates to silicone elastomers obtainable by crosslinking the above-described inventive hydrosilylatable compositions, especially the polyorganosiloxane compositions described.

The invention likewise relates to coatings, especially antiadhesive coatings, for example for producing release, backing and interleaving papers obtainable by crosslinking the above-described inventive hydrosilylatable compositions, especially the polyorganosiloxane compositions described.

The invention likewise relates to polysiloxane or organosilane compositions which are produced by the process according to the invention and are usable, for example, for producing dental imprints, adhesives, release liners, flat gaskets, sealants and coatings.

As is well known, the compounds (A) and (B) or (C) used in the inventive compositions are selected such that crosslinking is possible. For example, compound (A) has at least two aliphatically unsaturated radicals and siloxane (B) at least three Si-bonded hydrogen atoms, or compound (A) has at least three aliphatically unsaturated radicals and siloxane (B) at least two Si-bonded hydrogen atoms, or else, instead of compound (A) and (B), siloxane (C) is used, which has aliphatically unsaturated radicals and Si-bonded hydrogen atoms in the abovementioned ratios.

The compound (A) used in accordance with the invention may also be silicon-free organic compounds with preferably at least two aliphatically unsaturated groups, and also organosilicon compounds having preferably at least two aliphatically unsaturated groups. Examples of organic compounds which can be used as component (A) in the inventive compositions are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]-hepta-2,5-diene, 1,3-diisopropenylbenzene, vinyl-containing polybutadiene, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene, and 4,5-dimethyl-4,5-diethyl-1,7-octadiene, N,N'-methylenebis(acrylamide), 1,1,1-tris(hydroxymethyl)propane triacrylate, 1,1,1-tris(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)-trione, diallyl malonate, polyethylene glycol diacrylate, polyethylene glycol dimethacrylate, poly(propylene glycol) methacrylate.

However, the inventive silicone compositions preferably comprise, as constituent (A), an aliphatically unsaturated organosilicon compound, for which all aliphatically unsaturated organosilicon compounds used to date in addition-crosslinking compositions may be used, and also, for example, silicone block copolymers with urea segments, silicone block copolymers with amide segments and/or imide segments and/or ester amide segments and/or polystyrene segments and/or silarylene segments and/or carborane segments and silicone graft copolymers with ether groups.

The organosilicon compounds (A) used, which have SiC-bonded radicals with aliphatic carbon-carbon multiple bonds, are preferably linear or branched organopolysiloxanes composed of units of the average general formula (X)

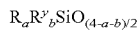

$$R_a R^y_b SiO_{(4-a-b)/2}$$ formula (X)

where
R may be the same or different and is an organic radical free of aliphatic carbon-carbon multiple bonds,
$R^y$ may be the same or different and is a monovalent, optionally substituted, SiC-bonded hydrocarbon radical with an aliphatic carbon-carbon multiple bond,
a is 0, 1, 2 or 3 and
b is 0, 1 or 2,
with the proviso that the sum of a+b is less than or equal to 3, and an average of at least 2 $R^y$ radicals are present per molecule.

The R radicals in the general formula (X) may be mono- or polyvalent radicals, in which case the polyvalent radicals, such as bivalent, trivalent and tetravalent radicals, may join a plurality of, for instance two, three or four, siloxy units of the general formula (X) to one another.

R includes especially the monovalent radicals —F, —Cl, —Br, —$OR^x$, —CN, —SCN, —NCO and SiC-bonded, optionally substituted hydrocarbon radicals which may be interrupted by oxygen atoms or the —C(O)— group, and also bivalent radicals Si-bonded on both sides of the general formula (X). $R^x$ is generally hydrogen or a monovalent, optionally substituted hydrocarbon radical having from 1 to 20 carbon atoms, preferably hydrogen, alkyl radicals and aryl radicals.

Examples of $R^x$ radicals are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, cycloalkyl radicals such as the cyclopropyl, cyclopentyl, cyclohexyl, cycloheptyl and methylcyclohexyl radicals, unsaturated radicals such as the allyl, 5-hexenyl, 7-octenyl, cyclohexenyl and styryl radicals, aryl radicals such as phenyl radicals, o-, m- or p-tolyl radicals, xylyl radicals and ethylphenyl radicals, and aralkyl radicals such as the benzyl radical and the α- and β-phenylethyl radicals.

Examples of halogenated $R^x$ radicals are haloalkyl radicals such as the 3,3,3-trifluoro-n-propyl radical, the 2,2,2,2',2',2'-hexafluoroisopropyl radical, the heptafluoroisopropyl radical, and haloaryl radicals such as the o-, m- or p-chlorophenyl radical.

$R^x$ is preferably hydrogen, alkyl radicals and aryl radicals, particular preference being given to hydrogen, the methyl radical and the ethyl radical.

If the R radicals are SiC-bonded, substituted hydrocarbon radicals, preferred substituents are halogen atoms, phosphorus-containing radicals, cyano radicals, —$OR^x$, —$NR^x$—, —$NR^x_2$, —$NR^x$—, —C(O)—$NR^x_2$, —C(O)—$NR^x_2$, —C(O)—$R^x$, —C(O)$OR^x$, —$SO_2$-Ph and —$C_6F_5$ where $R^x$ is as defined above and Ph is a phenyl radical.

Examples of R radicals are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical, cycloalkyl radicals such as the cyclopentyl, cyclohexyl, cycloheptyl and methylcyclohexyl radicals, aryl radicals such as the phenyl, naphthyl, anthryl and phenanthryl radicals, alkaryl radicals such as o-, m-, p-tolyl radicals, xylyl radicals and ethylphenyl radicals, and aralkyl radicals such as the benzyl radical, and the α- and the β-phenylethyl radicals.

Examples of substituted R radicals are haloalkyl radicals such as the 3,3,3-trifluoro-n-propyl radical, the 2,2,2,2',2',2'-hexafluoroisopropyl radical, the heptafluoroisopropyl radical, haloaryl radicals such as the o-, m- and p-chlorophenyl radical, —$(CH_2)_n$—$N(R^x)$ C(O)$NR^x_2$, —$(CH_2)_n$—C(O)$NR^x_2$, —$(CH_2)_n$—C(O) $R^x$, —$(CH_2)_n$—C(O)$OR^x$, —$(CH_2)_n$—C(O)$NR^x_2$, —$(CH_2)_n$—C(O)— $(CH_2)_m$—C(O)$CH_3$, —$(CH_2)_n$—$NR^x$—$(CH_2)_m$—$NR^x_2$, —$(CH_2)_n$—O—CO—$R^x$, —$(CH_2)_n$—O— $(CH_2)_m$—CH(OH)—$CH_2OH$, —$(CH_2)_n$ —$(OCH_2CH_2)_m$—$OR^x$, —$(CH_2)$—$SO_2$-Ph and —$(CH_2)_n$—O—$C_6F_5$, where $R^x$ is as defined above, n and m are identical or different integers from 0 to 10 and Ph denotes the phenyl radical.

Examples of R as bivalent radicals Si-bonded on both sides of the general formula (X) are those which derive from the above monovalent examples mentioned for the R radical by substitution of a hydrogen atom for an additional bond. Examples of such radicals are —$(CH_2)_n$—, —$CH(CH_3)$—, —$C(CH_3)_2$—, —$CH(CH_3)$—$CH_2$—, —$C_6H_4$—, —CH(Ph)—$CH_2$—, —$C(CF_3)_2$—, —$(CH_2)_n$—$C_6H_4$—$(CH_2)_n$—, —$(CH_2)_n$—$C_6H_4$—$C_6H_4$—$(CH_2)_n$—, —$(CH_2O)_m$—, —$(CH_2CH_2O)_m$—, —$(CH_2)_n$—$O_x$—$C_6H_4$—$SO_2$—$C_6H_4$—$O_x$—$(CH_2)_n$—, where x is 0 or 1, m and n are each as defined above and Ph is the phenyl radical.

The R radical is preferably a monovalent, SiC-bonded, optionally substituted hydrocarbon radical which has from 1 to 18 carbon atoms and is free of aliphatic carbon-carbon multiple bonds, more preferably a monovalent SiC-bonded hydrocarbon radical which has from 1 to 6 carbon atoms and is free of aliphatic carbon-carbon multiple bonds, especially the methyl or phenyl radical.

The $R^y$ radicals may be any groups amenable to an addition reaction (hydrosilylation) with an SiH-functional compound.

If the $R^y$ radicals are SiC-bonded, substituted hydrocarbon radicals, preferred substituents are halogen atoms, cyano radicals and —$OR^x$ where $R^x$ is as defined above.

The $R^y$ radicals are preferably alkenyl and alkynyl groups having from 2 to 16 carbon atoms, such as vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl and styryl radicals, particular preference being given to using vinyl, allyl and hexenyl radicals.

The molecular weight of constituent (A) may vary within wide limits, for instance between $10^2$ and $10^6$ g/mol. For example, constituent (A) may be a relatively low molecular weight alkenyl-functional oligosiloxane such as 1,3-divinyltetramethyldisiloxane, but may also be a highly polymerized polydimethylsiloxane having pendant or terminal Si-bonded vinyl groups, for example having a molecular weight of $10^5$ g/mol (number-average determined by means of NMR). Nor is the structure of the molecules forming constituent (A) fixed; in particular, the structure of a relatively high molecular weight, i.e. oligomeric or polymeric, siloxane may be linear, cyclic, branched or else resinous, network-like. Linear and cyclic polysiloxanes are preferably composed of units of the formula $R_3SiO_{1/2}$, $R^yR_2SiO_{1/2}$, $R^yRSiO_{2/2}$ and $R_2SiO_{2/2}$, where R and $R^y$ are each as defined above. Branched and network-like polysiloxanes additionally contain trifunctional and/or tetrafunctional units, preference being given to those of the formulae $RSiO_{3/2}$, $R^ySiO_{3/2}$ and $SiO_{4/2}$. It will be appreciated that it is also possible to use mixtures of different siloxanes which satisfy the criteria of constituent (A).

As component (A), particular preference is given to the use of vinyl-functional, substantially linear polydiorganosiloxanes having a viscosity of from 0.01 to 500,000 Pa·s, more preferably from 0.1 to 100,000 Pa·s, in each case at 25° C.

The organosilicon compounds (B) used may be all hydrogen-functional organosilicon compounds which have also been used to date in addition-crosslinkable compositions.

The organopolysiloxanes (B) used, which have Si-bonded hydrogen atoms, are preferably linear, cyclic or branched organopolysiloxanes composed of units of the average general formula (XI)

$$R_cH_dSiO_{(4-c-d)/2} \qquad \text{formula (XI)}$$

in which
R may be the same or different and is as defined above,
c is 0, 1, 2 or 3 and
d is 0, 1 or 2,
with the proviso that the sum of c+d is less than or equal to 3 and, on average, at least two Si-bonded hydrogen atoms are present per molecule.

The organopolysiloxane (B) used in accordance with the invention preferably contains Si-bonded hydrogen in the range from 0.04 to 1.7 percent by weight based on the total weight of the organopolysiloxane (B).

The molecular weight of constituent (B) may likewise vary within wide limits, for instance between $10^2$ and $10^6$ g/mol. For example, constituent (B) may be a relatively low molecular weight SiH-functional oligosiloxane, such as tetramethyldisiloxane, but also a highly polymerized polydimethylsiloxane having pendant or terminal SiH groups, or a silicone resin having SiH groups. Nor is the structure of the molecules which form constituent (B) fixed; in particular, the structure of a relatively high molecular weight, i.e., oligomeric or polymeric, SiH-containing siloxane may be linear, cyclic, branched or else resinous, network-like. Linear and cyclic polysiloxanes are preferably composed of units of the formula $R_3SiO_{1/2}$, $HR_2SiO_{1/2}$, $HRSiO_{2/2}$ and $R_2SiO_{2/2}$, where R is as defined above. Branched and network-like polysiloxanes additionally contain trifunctional and/or tetrafunctional units, preference being given to those of the formulae $RSiO_{3/2}$, $HSiO_{3/2}$ and $SiO_{4/2}$. It will be appreciated that it is also possible to use mixtures of different siloxanes which satisfy the criteria of constituent (B). In particular, the molecules which form constituent (B), in addition to the obligatory SiH groups, may optionally at the same time also contain aliphatically unsaturated groups. Particular preference is given to the use of low molecular weight SiH-functional compounds such as tetrakis(dimethylsiloxy)silane and tetramethylcyclotetrasiloxane, and also higher molecular weight, SiH-containing siloxanes such as poly(hydromethyl)siloxane and poly(dimethylhydromethyl)siloxane with a viscosity at 25° C. of from 10 to 10,000 mPa·s, or analogous SiH-containing compounds in which some of the methyl groups have been replaced by 3,3,3-trifluoropropyl or phenyl groups.

Constituent (B) is present in the inventive crosslinkable overall silicone compositions preferably in such an amount that the molar ratio of SiH groups to aliphatically unsaturated groups is from 0.1 to 20, more preferably between 1.0 and 5.0.

The components (A) and (B) used in accordance with the invention are commercial products or preparable by processes common in chemistry.

Instead of component (A) and (B), the inventive compositions may comprise organopolysiloxanes (C) which have aliphatic carbon-carbon multiple bonds and Si-bonded hydrogen atoms.

If siloxanes (C) are used, they are preferably those composed of units of the formulae $$R_gSiO_{4-g/2}, R_hR^ySiO_{3-h/2} \text{ and } R_iHSiO_{3-i/2},$$

where R and $R^y$ are each as defined above,
g is 0, 1, 2 or 3,
h is 0, 1 or 2 and
i is 0, 1 or 2,
with the proviso that at least 2 $R^y$ radicals and at least 2 Si-bonded hydrogen atoms are present per molecule.

Examples of organopolysiloxanes (C) are those composed of $SiO_{4/2}$, $R_3SiO_{1/2}$, $R_2R^ySiO_{1/2}$ and $R_2HSiO_{1/2}$ units, so-called MQ resins which may additionally contain $RSiO_{3/2}$ and $R_2SiO$ units, and also linear organopolysiloxanes substantially consisting of $R_2R^ySiO_{1/2}$, $R_2SiO$ and RHSiO units where R and $R^y$ are each as defined above.

The organopolysiloxanes (C) preferably have an average viscosity of from 0.01 to 500,000 Pa·s, more preferably from 0.1 to 100,000 Pa·s, in each case at 25° C.

Organopolysiloxanes (C) are preparable by methods common in chemistry.

Apart from components (A) to (D), the inventive curable compositions may also comprise all further substances which have also been used to date to produce addition-crosslinkable materials.

Examples of reinforcing fillers which may be used as component (E) in the inventive materials are fumed or precipitated silicas having BET surface areas of at least 50 $m^2/g$, and also carbon blacks and activated carbons such as furnace black and acetylene black, preference being given to fumed and precipitated silicas having BET surface areas of at least 50 $m^2/g$.

These silica fillers may have hydrophilic character or be hydrophobized by known processes. When hydrophilic fillers are incorporated, the addition of a hydrophobizing agent is required.

The content in the inventive crosslinkable material of actively reinforcing filler (E) is in the range from 0 to 70% by weight, preferably from 0 to 50% by weight.

The inventive compositions, especially the polyorganosiloxane materials, may optionally comprise, as constituent (F), further additives in a proportion of up to 70% by weight, preferably from 0.0001 to 40% by weight. These additives may, for example, be inactive fillers, resinous polyorganosiloxanes other than siloxanes (A), (B) and (C), dispersing assistants, solvents, adhesion promoters, pigments, dyes, plasticizers, organic polymers, heat stabilizers, etc. They include additives such as quartz flour, diatomaceous earth, clays, chalk, lithopone, carbon blacks, graphite, metal oxides, metal carbonates and sulfates, metal salts of carboxylic acids, metal dusts, fibers such as glass fibers, polymer fibers, polymer powders, dyes, pigments, etc. The inventive compositions, especially the organopolysiloxane materials, can be prepared by known processes, for example by homogeneously mixing the individual components. The sequence is as desired, but preference is given to the homogeneous mixing of the inventive ruthenium catalyst (D) with a mixture of (A) and (B) or (C), and optionally (E) and (F). The ruthenium catalyst (D) used in accordance with the invention can be incorporated as a solid substance or as a so-called batch—mixed homogeneously with a small amount of (A) or (A) with (E). The mixing is effected, depending on the viscosity of (A), for example, with a stirrer, in a dissolver, on a roller or in a kneader.

The examples which follow serve to illustrate the inventive use, the process according to the invention and the inventive compositions, and should in no way at all be considered as a restriction.

EXAMPLES

Preparation of the Catalysts

Example 1

Synthesis of (p-cymene)Ru(H)$_2$[(SiMe$_2$O)$_x$SiMe$_3$]$_2$ (x≈14)

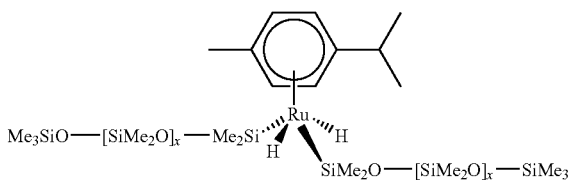

A mixture of 50 mg (0.08 mmol) of [(p-cymene)RuCl$_2$]$_2$ in 10 ml of tetrahydrofuran is admixed with 740 mg (approx. 0.67 mmol) of HMe$_2$Si—[O—SiMe$_2$]$_x$—OSiMe$_3$ and the mixture is heated to 80° C. for 15 h. After cooling, all volatile constituents are removed under reduced pressure. The residue is taken up in 20 ml of n-pentane and filtered through Florisil, and the filtrate is concentrated by evaporation under reduced pressure. There remains a brown oil. Yield 243 mg (62%).

$^1$H NMR (300 MHz, C$_6$D$_6$): d=5.52 (s, br, 4H, C$_6$H$_4$), 2.44 [sept, 1H, CH(CH$_3$)$_2$], 2.01 (s, 3H, CH$_3$), 1.11 [d, 6H, (CH$_3$)$_2$CH], 0.70 [s, 12H, (CH$_3$)$_2$Si—Ru], 0.24-0.17 [(CH$_3$)$_2$Si—O, SiMe$_3$], −13.18 ppm (s, 2H, H—Ru).

Example 2

Synthesis of (p-cymene)Ru(h$^4$-TMDVS)

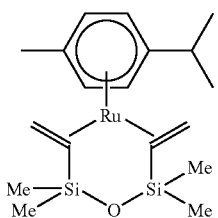

A mixture of 995 mg (1.63 mmol) of [(p-cymene)RuCl$_2$]$_2$, 958 mg (9.03 mmol) of Na$_2$CO$_3$ (anhydrous) and 5.75 g (30.8 mmol) of divinyltetramethyldisiloxane in 50 ml of ethanol is heated under reflux at 90° C. for 4 h. After cooling, all volatile constituents are removed under reduced pressure. The residue is admixed with 50 ml of n-heptane, extracted at 40° C. for 1 h and filtered while warm through Celite in a preheated filter. The filtrate is concentrated to a volume of 5 ml and subjected to column chromatography using Al$_2$O$_3$ (neutral, activity level I, eluent: n-pentane). The evaporative concentration of the eluted yellow zone affords a yellow-orange oil. Yield: 346 mg (25%).

$^1$H NMR (300 MHz, C$_6$D$_6$): d=4.39 (s, br, 4H, C$_6$H$_4$), 3.84-2.64 (m, 6H, H$_2$C=CH—Si), 2.30 [sept, 1H, CH(CH$_3$)$_2$], 1.79 (s, 3H, CH$_3$), 1.07 [d, 6H, (CH$_3$)$_2$CH], 0.46 (s, 6H, CH$_3$Si), 0.38 ppm (s, 6H, CH$_3$Si)

Study of the Catalytic Properties

Example 3

Hydrosilylation of HMe$_2$SiO—[SiMe$_2$O]$_x$—SiMe$_2$H (x≈13) (H-polymer 13) with 3-vinylheptamethyltrisiloxane and the catalyst (p-cymene)Ru(H)$_2$[(SiMe$_2$O)$_x$—SiMe$_3$]$_2$ (from Example 1) at 160° C.

A mixture of 2.5 g (approx. 2.63 mmol) of H-polymer 13 and 1.44 g (5.78 mmol) of 3-vinylheptamethyltrisiloxane is admixed with 28.4 mg of (p-cymene)Ru(H)$_2$[(SiMe$_2$O)$_x$—SiMe$_3$]$_2$ (approx. 300 ppm of Ru) (obtainable by a process according to Example 1) and stirred at 160° C. The hydrosilylation reaction (conversion, selectivity, yield) is analyzed by $^1$H NMR.

| Reaction time | Conversion [%] | Selectivity [%] | Yield [%] |
|---|---|---|---|
| 15 min. | 89 | 91 | 81 |
| 1 h | 97 | 89 | 87 |

Comparative Example 1

Ru-Arene Catalyst without Si-Substituted Ligand; Hydrosilylation of HMe$_2$SiO—[SiMe$_2$O]$_x$—SiMe$_2$H (x≈13) (H-polymer 13) with 3-vinylheptamethyltrisiloxane and the catalyst [(p-cymene)-RuCl$_2$]$_2$ at 160° C.

A mixture of 2.51 g (approx. 2.63 mmol) of H-polymer 13 and 1.44 g (5.78 mmol) of 3-vinylheptamethyltrisiloxane is admixed with 4.6 mg of [(p-cymene)RuCl$_2$]$_2$ (384 ppm of Ru), and stirred at 160° C. The hydrosilylation reaction (conversion, selectivity, yield) is analyzed by $^1$H NMR.

| Reaction time | Conversion [%] | Selectivity [%] | Yield [%] |
|---|---|---|---|
| 15 min. | 84 | 63 | 53 |
| 1 h | 93 | 66 | 61 |

Comparative Example 2

Pt catalyst; Hydrosilylation of HMe$_2$SiO—[SiMe$_2$O]$_x$—SiMe$_2$H (x≈13) (H-polymer 13) with 3-vinylheptamethyltrisiloxane and the Karstedt Catalyst Pt$_2$(TVDMS)$_3$ at 120° C.

A mixture of 2.51 g (approx. 2.63 mmol) of H-polymer 13 and 1.44 g (5.78 mmol) of 3-vinylheptamethyltrisiloxane is admixed with 19 μl of a solution (2% Pt) of the Karstedt catalyst in xylene (96 ppm of Pt), and stirred at 120° C. The hydrosilylation reaction (conversion, selectivity, yield) is analyzed by $^1$H NMR.

| Reaction time | Conversion [%] | Selectivity [%] | Yield [%] |
|---|---|---|---|
| 15 min. | 100 | 91 | 91 |

Example 4

Hydrosilylation of HMe$_2$SiO—[SiMe$_2$O]$_x$—SiMe$_2$H (x≈13) (H-polymer 13) with 3-vinylheptamethyltrisiloxane and the catalyst (p-cymene)Ru(h$^4$-TMDVS) (from Example 2) at 120° C.

A mixture of 2.5 g (approx. 2.63 mmol) of H-polymer 13 and 1.44 g (5.78 mmol) of 3-vinylheptamethyltrisiloxane is admixed with 5.1 mg of (p-cymene)Ru(h$^4$-TMDVS) (approx. 300 ppm of Ru) (obtainable by a process according to Example 2) and stirred at 120° C. The hydrosilylation reaction (conversion, selectivity, yield) is analyzed by $^1$H NMR.

| Reaction time | Conversion [%] | Selectivity [%] | Yield [%] |
|---|---|---|---|
| 15 min. | 67 | 73 | 49 |
| 1 h | 94 | 72 | 68 |

Example 5

Crosslinking of an α,ω-divinylpolydimethylsiloxane with an SiH-functional polysiloxane at 120° C.

10 g of an α,ω-divinylpolydimethylsiloxane, viscosity η=500 mPa·s (Wacker VIPO 500) are admixed with the Ru catalyst (300 ppm of Ru based on the total mass of the mixture), mixed vigorously in a round-bottom flask and admixed with 250 mg of an SiH-functional polysiloxane of the formula Me$_3$SiO—[Si(H)MeO]$_{48}$—SiMe$_3$ (Wacker V24 crosslinker) and mixed vigorously once again.

The mixture is stirred in a preheated oil bath at 120° C. and 500 rpm. The time until the gelation has progressed to such an extent that stirring with a magnetic stirrer bar is no longer completely possible is determined.

| Catalyst | Gelation time |
|---|---|
| (p-cymene)Ru(H)$_2$(SiEt$_3$)$_2$ | 11 min. 20 s |
| (p-cymene)Ru(H)$_2$[(SiMe$_2$O)$_x$—SiMe$_3$]$_2$ | 8 min. 20 s |
| (p-cymene)Ru(h$^4$-TMDVS) | 4 min. 10 s |
| Comparative Example | |
| [(p-cymene)RuCl$_2$]$_2$ | 38 min. |
| [Pt$_2$(TMDVS)$_3$], "Karstedt catalyst" (100 ppm Pt) | <5 s |

Example 6

Crosslinking of an α,ω-divinylpolydimethylsiloxane with an SiH-functional polysiloxane in thin layers at 120° C.

The mixture from Example 3 is applied to a microscope slide as a layer with a doctor blade (60µ) and heated on a heating bench at 120° C.

The quality of the crosslinking is determined by a rub-off test, which is carried out after certain times, with a rating according to the following criteria:
6: fluid system
5: fluid system with partially crosslinked zones
4: crosslinked layer, destroyed after 1 finger rub
3: crosslinked layer, destroyed after 2-4 finger rubs
2: crosslinked layer, destroyed after >4 finger rubs
1: crosslinked layer which cannot be destroyed by finger rubs

| Catalyst | Microscope slide |
|---|---|
| (p-cymene)Ru(H)$_2$[(SiMe$_2$O)$_x$—SiMe$_3$]$_2$ | 1 min.: 5 |
| | 5 min.: 4 |
| | 10 min.: 3 |
| | 20 min.: 2 |
| (p-cymene)Ru(H)$_2$(SiEt$_3$)$_2$ | 1 min.: 6 |
| | 5 min.: 5 |
| | 10 min.: 4 |
| | 20 min.: 3 |
| Comparative Examples | |
| [(p-cymene)RuCl$_2$]$_2$ | 1 min.: 6 |
| | 5 min.: 5 |
| | 10 min.: 5 |
| | 20 min.: 5 |
| Ru(CO)$_3$(PPh$_3$)$_2$ | 1-20 min.: 6 |

The invention claimed is:
1. A silicophilic ligand-containing Ru compound of the formulae (1a), (2a), (3(a-d)), 4, or 5

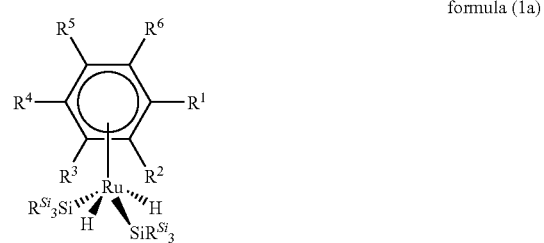

formula (1a)

where
the two SiR$^{Si}_3$ radicals are the same or different and each R$^{Si}_3$ independently is a radical selected from the group consisting of triaryl, dialkylhalogen, diarylhalogen, alkyl(aryl)halogen, alkyldihalogen, aryldihalogen, trihalogen, dialkyl(alkoxy), diaryl(alkoxy), alkyl(aryl) alkoxy, alkyl(dialkoxy), aryl(dialkoxy), trialkoxy, Me(OSiMe$_3$)$_2$, Ph(OSiMe$_3$)$_2$, (OSiMe$_3$)$_3$, (dialkylsiloxy)$_n$-SiMe$_3$, (diarylsiloxy)$_n$-SiMe$_3$ and [alkyl(aryl)siloxy]$_n$-SiMe$_3$, where n is from 1 to 500; and
the R$^1$ to R$^6$ radicals are each independently hydrogen, alkyl, aryl alkoxy, SiR$^{Si}_3$ or OSiR$^{Si}_3$, wherein the alkyl, aryl and alkoxy radicals are optionally substituted by SiR$^{Si}_3$ and OSiR$^{Si}_3$ radicals where R$^{Si}_3$ is optionally trialkyl; and two adjacent R$^1$ to R$^6$ radicals optionally form a ring structure;

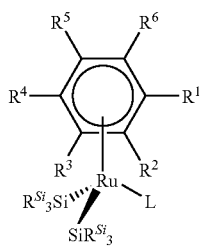

formula (2a)

where the two SiR$^{Si}_3$ radicals are as in formula (1a), the R$^1$ and R$^6$ radicals are each independently hydrogen, alkyl, aryl, alkoxy, SiR$^{Si}_3$ or OSiR$^{Si}_3$, with the proviso that the alkyl, aryl and alkoxy radicals are optionally substituted by SiR$^{Si}_3$ and OSiR$^{Si}_3$ radicals where R$^{Si}_3$ is optionally trihalogen, two adjacent R$^1$ and R$^6$ radicals optionally form a ring structure, and L is an uncharged 2-electron donor ligand;

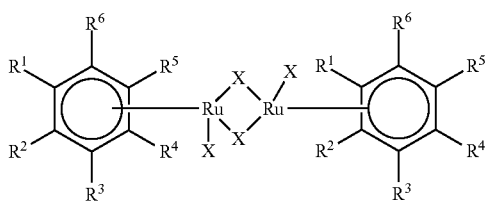

formula (3a)

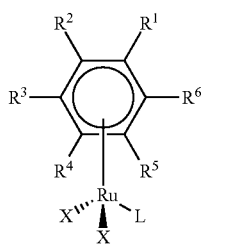

formula (3b)

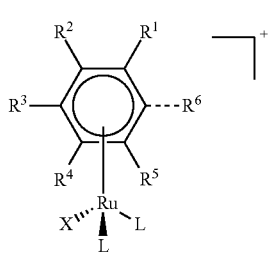

formula (3c)

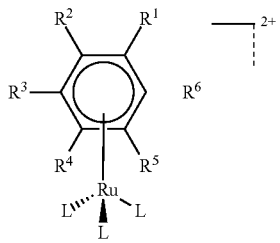

formula (3d)

where

X is an anionic ligand; and

L is an uncharged 2-electron donor ligand; and

L and X are optionally joined to one another and, together with the ruthenium atom to which they are bonded, and optionally form a ring which optionally contains further atoms, the R$^1$ to R$^6$ radicals are each independently hydrogen, alkyl, aryl, alkoxy, halogen, SiR$^{Si}_3$ or OSiR$^{Si}_3$, where the alkyl, aryl and alkoxy radicals are optionally substituted by SiR$^{Si}_3$ and OSiR$^{Si}_3$ radicals, and with the further proviso that at least one of the R$^1$ to R$^6$ radicals is an SiR$^{Si}_3$ radical, an OSiR$^{Si}_3$ radical or an alkyl, aryl or alkoxy radical substituted by SiR$^{Si}_3$, OSiR$^{Si}_3$; and R$^{Si}_3$ in the SiR$^{Si}_3$ and/or OSiR$^{Si}_3$ radicals are each independently trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl) alkoxy, alkyl(dialkoxy), aryl(dialkoxy), trialkoxy, Me(OSiMe$_3$)$_2$, Ph(OSiMe$_3$)$_2$, (OSiMe$_3$)$_3$, (dialkylsiloxy)$_n$-SiMe$_3$, (diarylsiloxy)$_n$-SiMe$_3$ or [alkyl(aryl)siloxy]$_n$-SiMe$_3$, where n is from 1 to 500;

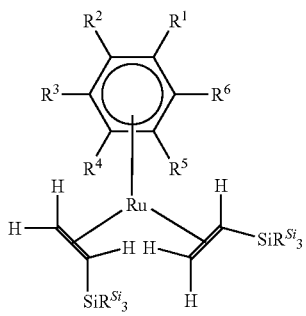

formula (4)

where the two SiR$^{Si}_3$ radicals are as defined in formula (1a);

the two SiR$^{Si}_3$ radicals are optionally joined to one another via an R$^{Si}$ substituent; and the R$^1$ to R$^6$ radicals are each independently hydrogen, alkyl, aryl, alkoxy, SiR$^{Si}_3$ or OSiR$^{Si}_3$, wherein the alkyl, aryl and alkoxy radicals are optionally substituted by SiR$^{Si}_3$ and OSiR$^{Si}_3$ radicals; and two adjacent R$^1$ to R$^6$ radicals optionally form a ring structure;

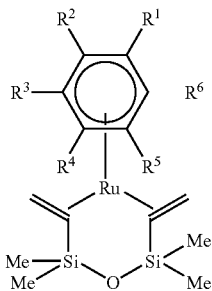

formula (5)

where
the $R^1$ to $R^6$ radicals are each independently hydrogen, alkyl, aryl, alkoxy, $SiR^{Si}_3$ and $OSiR^{Si}_3$, where the alkyl, aryl and alkoxy radicals are optionally substituted by $SiR^{Si}_3$ and $OSiR^{Si}_3$ radicals; and where $R^{Si}_3$ is trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, (dialkylsiloxy)$_n$-$SiMe_3$, (diarylsiloxy)$_n$-$SiMe_3$ or [alkyl(aryl)siloxy]$_n$$SiMe_3$, where n is from 1 to 500; and two adjacent $R^1$ to $R^6$ radicals optionally form a ring structure.

2. A compound of claim 1, wherein when $R^1$ to $R^6$ are radicals substituted by $SiR^{Si}_3$ and $OSiR^{Si}_3$ radicals, $R^1$ to $R^6$ are selected from the group consisting of —$(CH_2)_n$—$SiR^{Si}_3$, —O—$SiR^{Si}_3$, —$O(CH_2)_m$—$SiR^{Si}_3$, —$(CH_2)_m$—$OSiR^{Si}_3$ and —$O(CH_2)_m$—$OSiR^{Si}_3$, where m is an integer of 1 to 3.

3. A process for hydrosilylation, comprising hydrosilylating a compound containing at least one aliphatically unsaturated carbon-carbon bond with a compound containing at least one silicon-bonded hydrogen, in the presence of at least one ruthenium hydrosilylation catalyst selected from the group consisting of ruthenium complexes which have, in their ligand sphere, at least one $\eta^6$-bonded arene ligand and a silyl ligand; ruthenium complexes which have, in their ligand sphere, at least one $\eta^6$-bonded arene ligand to which is bonded a silyl or siloxy radical directly or via a spacer, and ruthenium complexes which have, in their ligand sphere, at least one $\eta^6$-bonded arene ligand and at least one further ligand to which is bonded a silyl or siloxy radical directly or via a spacer.

4. The process of claim 3, wherein at least one hydrosilylation catalyst is a compound of the formulae (1a), (2a), (3(a-d)), 4, or 5

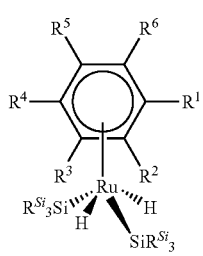

formula (1a)

where
the two $SiR^{Si}_3$ radicals are the same or different and each $R^{Si}_3$ independently is a radical selected from the group consisting of triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, (dialkylsiloxy)$_n$-$SiMe_3$, (diarylsiloxy)$_n$-$SiMe_3$ and [alkyl(aryl)siloxy]$_n$-$SiMe_3$, where n is from 1 to 500; and the $R^1$ to $R^6$ radicals are each independently hydrogen, alkyl, aryl alkoxy, $SiR^{Si}_3$ or $OSiR^{Si}_3$, wherein the alkyl, aryl and alkoxy radicals are optionally substituted by $SiR^{Si}_3$ and $OSiR^{Si}_3$ radicals where $R^{Si}_3$ is optionally trialkyl; and two adjacent $R^1$ to $R^6$ radicals optionally form a ring structure;

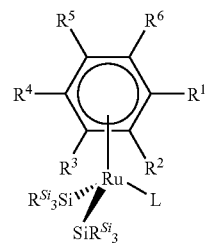

formula (2a)

where
the two $SiR^{Si}_3$ radicals are as in formula (1a),
the $R^1$ and $R^6$ radicals are each independently hydrogen, alkyl, aryl, alkoxy, $SiR^{Si}_3$ or $OSiR^{Si}_3$, with the proviso that the alkyl, aryl and alkoxy radicals are optionally substituted by $SiR^{Si}_3$ and $OSiR^{Si}_3$ radicals where $R^{Si}_3$ is optionally trihalogen, two adjacent $R^1$ and $R^6$ radicals optionally form a ring structure, and L is an uncharged 2-electron donor ligand;

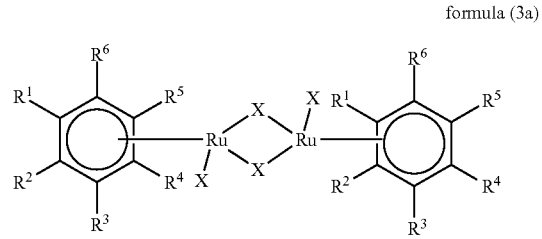

formula (3a)

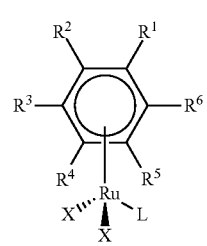

formula (3b)

formula (3c)

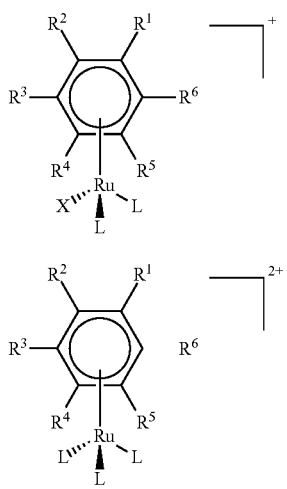

formula (3d)

where
X is an anionic ligand; and
L is an uncharged 2-electron donor ligand; and
L and X are optionally joined to one another and, together with the ruthenium atom to which they are bonded, and optionally form a ring which optionally contains further atoms,
the $R^1$ to $R^6$ radicals are each independently hydrogen, alkyl, aryl, alkoxy, halogen, $SiR^{Si}_3$ or $OSiR^{Si}_3$, where the alkyl, aryl and alkoxy radicals are optionally substituted by $SiR^{Si}_3$ and $OSiR^{Si}_3$ radicals, and with the further proviso that at least one of the $R^1$ to $R^6$ radicals is an $SiR^{Si}_3$ radical, an $OSiR^{Si}_3$ radical or an alkyl, aryl or alkoxy radical substituted by $SiR^{Si}_3$, $OSiR^{Si}_3$; and
$R^{Si}_3$ in the $SiR^{Si}_3$ and/or $OSiR^{Si}_3$ radicals are each independently trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, (dialkylsiloxy)$_n$-SiMe$_3$, (diarylsiloxy)$_n$-SiMe$_3$ or [alkyl(aryl)siloxy]$_n$-SiMe$_3$, where n is from 1 to 500;

formula (4)

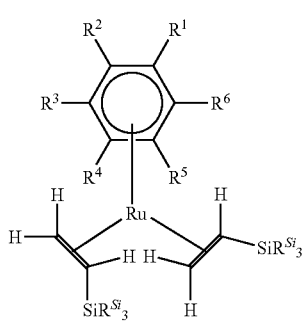

where
the two $SiR^{Si}_3$ radicals are as defined in formula (1a);
the two $SiR^{Si}_3$ radicals are optionally joined to one another via an $R^{Si}$ substituent; and
the $R^1$ to $R^6$ radicals are each independently hydrogen, alkyl, aryl, alkoxy, $SiR^{Si}_3$ or $OSiR^{Si}_3$, wherein the alkyl, aryl and alkoxy radicals are optionally substituted by $SiR^{Si}_3$ and $OSiR^{Si}_3$ radicals; and two adjacent $R^1$ to $R^6$ radicals optionally form a ring structure;

formula (5)

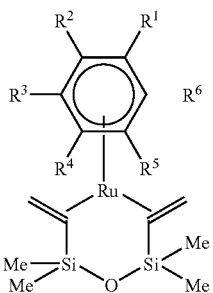

where
the $R^1$ to $R^6$ radicals are each independently hydrogen, alkyl, aryl, alkoxy, $SiR^{Si}_3$ and $OSiR^{Si}_3$, where the alkyl, aryl and alkoxy radicals are optionally substituted by $SiR^{Si}_3$ and $OSiR^{Si}_3$ radicals; and
where $R^{Si}_3$ is trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, (dialkylsiloxy)$_n$-SiMe$_3$, (diarylsiloxy)$_n$-SiMe$_3$ or [alkyl(aryl)siloxy]$_n$-SiMe$_3$, where n is from 1 to 500; and
two adjacent $R^1$ to $R^6$ radicals optionally form a ring structure.

5. A hydrosilylatable composition comprising
(A) a compound with at least one aliphatically unsaturated carbon-carbon bond,
(B) a compound with at least one silicon-hydrogen bond and
(D) a ruthenium compound selected from the group consisting of ruthenium complexes which have, in their ligand sphere, at least one $\eta^6$-bonded arene ligand and a silyl ligand; ruthenium complexes which have, in their ligand sphere, at least one $\eta^6$-bonded arene ligand to which is bonded a silyl or siloxy radical directly or via a spacer, and ruthenium complexes which have, in their ligand sphere, at least one $\eta^6$-bonded arene ligand and at least one further ligand to which is bonded a silyl or siloxy radical directly or via a spacer.

6. The hydrosilylatable composition of claim 5, wherein at least one ruthenium compound of component (D) is a ruthenium compound of the formulae (1a), (2a), (3(a-d)), 4, or 5 formula (1a)

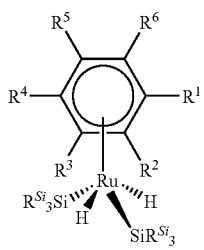

where
the two $SiR^{Si}_3$ radicals are the same or different and each $R^{Si}_3$ independently is a radical selected from the group consisting of triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, $(dialkylsiloxy)_n-SiMe_3$, $(diarylsiloxy)_n-SiMe_3$ and $[alkyl(aryl)siloxy]_n-SiMe_3$, where n is from 1 to 500; and the $R^1$ to $R^6$ radicals are each independently hydrogen, alkyl, aryl alkoxy, $SiR^{Si}_3$ or $OSiR^{Si}_3$, wherein the alkyl, aryl and alkoxy radicals are optionally substituted by $SiR^{Si}_3$ and $OSiR^{Si}_3$ radicals where $R^{Si}_3$ is optionally trialkyl; and two adjacent $R^1$ to $R^6$ radicals optionally form a ring structure;

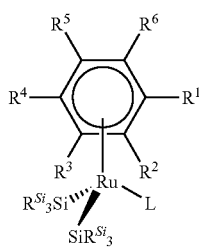

formula (2a)

where the two $SiR^{Si}_3$ radicals are as in formula (1a), the $R^1$ and $R^6$ radicals are each independently hydrogen, alkyl, aryl, alkoxy, $SiR^{Si}_3$ or $OSiR^{Si}_3$, with the proviso that the alkyl, aryl and alkoxy radicals are optionally substituted by $SiR^{Si}_3$ and $OSiR^{Si}_3$ radicals where $R^{Si}_3$ is optionally trihalogen, two adjacent $R^1$ and $R^6$ radicals optionally form a ring structure, and L is an uncharged 2-electron donor ligand;

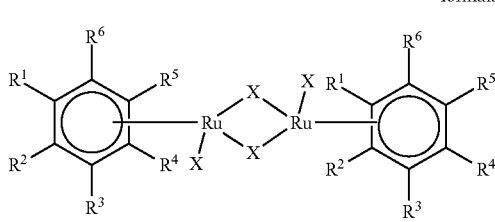

formula (3a)

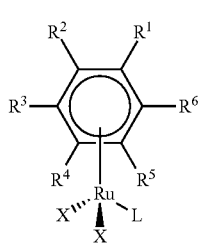

formula (3b)

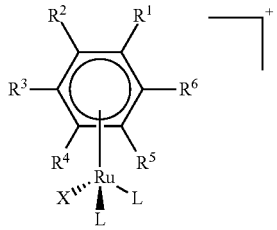

formula (3c)

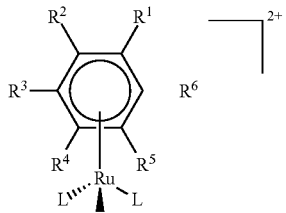

formula (3d)

where

X is an anionic ligand; and

L is an uncharged 2-electron donor ligand; and

L and X are optionally joined to one another and, together with the ruthenium atom to which they are bonded, and optionally form a ring which optionally contains further atoms, the $R^1$ to $R^6$ radicals are each independently hydrogen, alkyl, aryl, alkoxy, halogen, $SiR^{Si}_3$ or $OSiR^{Si}_3$, where the alkyl, aryl and alkoxy radicals are optionally substituted by $SiR^{Si}_3$ and $OSiR^{Si}_3$ radicals, and with the further proviso that at least one of the $R^1$ to $R^6$ radicals is an $SiR^{Si}_3$ radical, an $OSiR^{Si}_3$ radical or an alkyl, aryl or alkoxy radical substituted by $SiR^{Si}_3$, $OSiR^{Si}_3$; and $R^{Si}_3$ in the $SiR^{Si}_3$ and/or $OSiR^{Si}_3$ radicals are each independently trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, $(dialkylsiloxy)_n-SiMe_3$, $(diarylsiloxy)_n-SiMe_3$ or $[alkyl(aryl)siloxy]_n-SiMe_3$, where n is from 1 to 500;

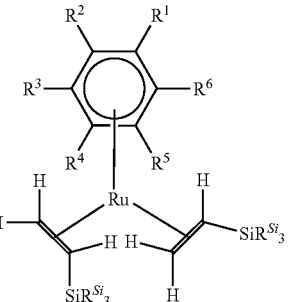

formula (4)

where the two $SiR^{Si}_3$ radicals are as defined in formula (1a);

the two $SiR^{Si}_3$ radicals are optionally joined to one another via an $R^{Si}$ substituent; and the $R^1$ to $R^6$ radicals are each independently hydrogen, alkyl, aryl, alkoxy, $SiR^{Si}_3$ or $OSiR^{Si}_3$, wherein the alkyl, aryl and alkoxy radicals are optionally substituted by $SiR^{Si}_3$ and $OSiR^{Si}_3$ radicals; and two adjacent $R^1$ to $R^6$ radicals optionally form a ring structure;

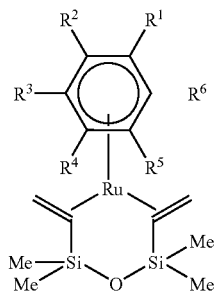

formula (5)

where
the $R^1$ to $R^6$ radicals are each independently hydrogen, alkyl, aryl, alkoxy, $SiR^{Si}_3$ and $OSiR^{Si}_3$, where the alkyl, aryl and alkoxy radicals are optionally substituted by $SiR^{Si}_3$ and $OSiR^{Si}_3$ radicals; and where $R^{Si}_3$ is trialkyl, triaryl, dialkylhalogen, diarylhalogen, alkyl(aryl)halogen, alkyldihalogen, aryldihalogen, trihalogen, dialkyl(alkoxy), diaryl(alkoxy), alkyl(aryl)alkoxy, alkyl(dialkoxy), aryl(dialkoxy), trialkoxy, $Me(OSiMe_3)_2$, $Ph(OSiMe_3)_2$, $(OSiMe_3)_3$, (dialkylsiloxy)$_n$-$SiMe_3$, (diarylsiloxy)$_n$-$SiMe_3$ or [alkyl(aryl)siloxy]$_n$-$SiMe_3$, where n is from 1 to 500; and two adjacent $R^1$ to $R^6$ radicals optionally form a ring structure.

7. A silicone elastomer obtained by crosslinking a hydrosilylatable composition of claim 5.

8. A coating obtained by crosslinking a hydrosilylatable composition of claim 5.

\* \* \* \* \*